United States Patent [19]

Baldwin

[11] Patent Number: 5,436,722

[45] Date of Patent: Jul. 25, 1995

[54] DEVICE FOR OPTIMALLY ILLUMINATE BOTTLES FOR BOTTOM INSPECTION

[75] Inventor: Leo B. Baldwin, Horseheads, N.Y.

[73] Assignee: Emhart Glass Machinery Investments Inc., Wilmington, Del.

[21] Appl. No.: 36,758

[22] Filed: Mar. 25, 1993

[51] Int. Cl.⁶ .............................................. G01N 21/90
[52] U.S. Cl. .................... 356/240; 250/223 B; 356/418
[58] Field of Search ............... 356/239, 240, 418, 419, 356/428; 250/223 B

[56] References Cited

U.S. PATENT DOCUMENTS

| | | | |
|---|---|---|---|
| 4,428,673 | 1/1984 | Yoshida | 356/240 |
| 4,500,203 | 2/1985 | Bieringer | 356/240 |
| 4,943,713 | 7/1990 | Yoshida | 356/240 |
| 4,959,537 | 9/1990 | Kimoto et al. | 356/240 |
| 4,967,070 | 10/1990 | Ringlien et al. | 250/223 B |
| 5,141,110 | 8/1992 | Trischan et al. | 356/240 |
| 5,349,435 | 9/1994 | Hall et al. | 356/240 |

Primary Examiner—Robert P. Limanek
Assistant Examiner—David B. Hardy
Attorney, Agent, or Firm—Spencer T. Smith

[57] ABSTRACT

A machine for inspecting the bottom of a glass container having an opening at the top thereof comprising deliverance of a glass container to an inspection station, the inspection station including a two dimensional camera having an imaging surface, viewing the bottom of the glass container through the opening thereof and focusing the viewed bottom on the imaging surface, computer for evaluating the viewed bottom imaged on the imaging surface and for illuminating the bottom of the glass container including a source of light for collimating light from the light source, diffusing the collimated light including two glass sheets each having a ground surface, the sheet being selectively locatable to define at least two spacings between the ground surface.

6 Claims, 2 Drawing Sheets

DEVICE FOR OPTIMALLY ILLUMINATE BOTTLES FOR BOTTOM INSPECTION

PURPOSE OF INVENTION

The purpose of this device is to optimally illuminate the bottom of a glass container such as a bottle which is under automated inspection. The detection of flaws in the bottom of a bottle depend in part in the quality of the illumination of the base. The purpose of this invention is to control the structure and spectrum of the light source so as to permit the inspection of bottles which would be difficult or impossible to inspect by current methods with existing light sources.

PRIOR ART

Several companies currently produce bottom inspection machines and the principle of operation is common to all of them. A bottle handling device presents a bottle to the inspection station which consists of a lens and camera situated above the bottle, looking down at the bottom of the bottle through the neck opening of the bottle. The bottom of the bottle is in turn illuminated from below by a diffuse light source which is sufficiently large to illuminate the entire bottom of the bottle.

Typically the light source is strobed to freeze the motion of the bottle, but the light source may be continuous if the camera is capable of shuttered operation. Strobed light sources typically consist of gas discharge tubes or light emitting diodes behind a diffusing element such as opal glass or the sheet plastic equivalent. Non-strobed cameras typically consist of fluorescent or incandescent lamps behind a similar diffusing element. It is common to use multiple light sources to increase the diffusion and uniformity of the light source with both strobed and continuous light sources, It is accordingly an object of the present invention to provide a device which will optimally illuminate bottles for bottom inspection, Other objects and advantages of the present invention will become apparent from the following portion of this specification and from the accompanying drawings which illustrate in accordance with the mandate of the patent statutes a presently preferred embodiment incorporating the principles of the invention.

Referring to the drawings.

Figure 1:
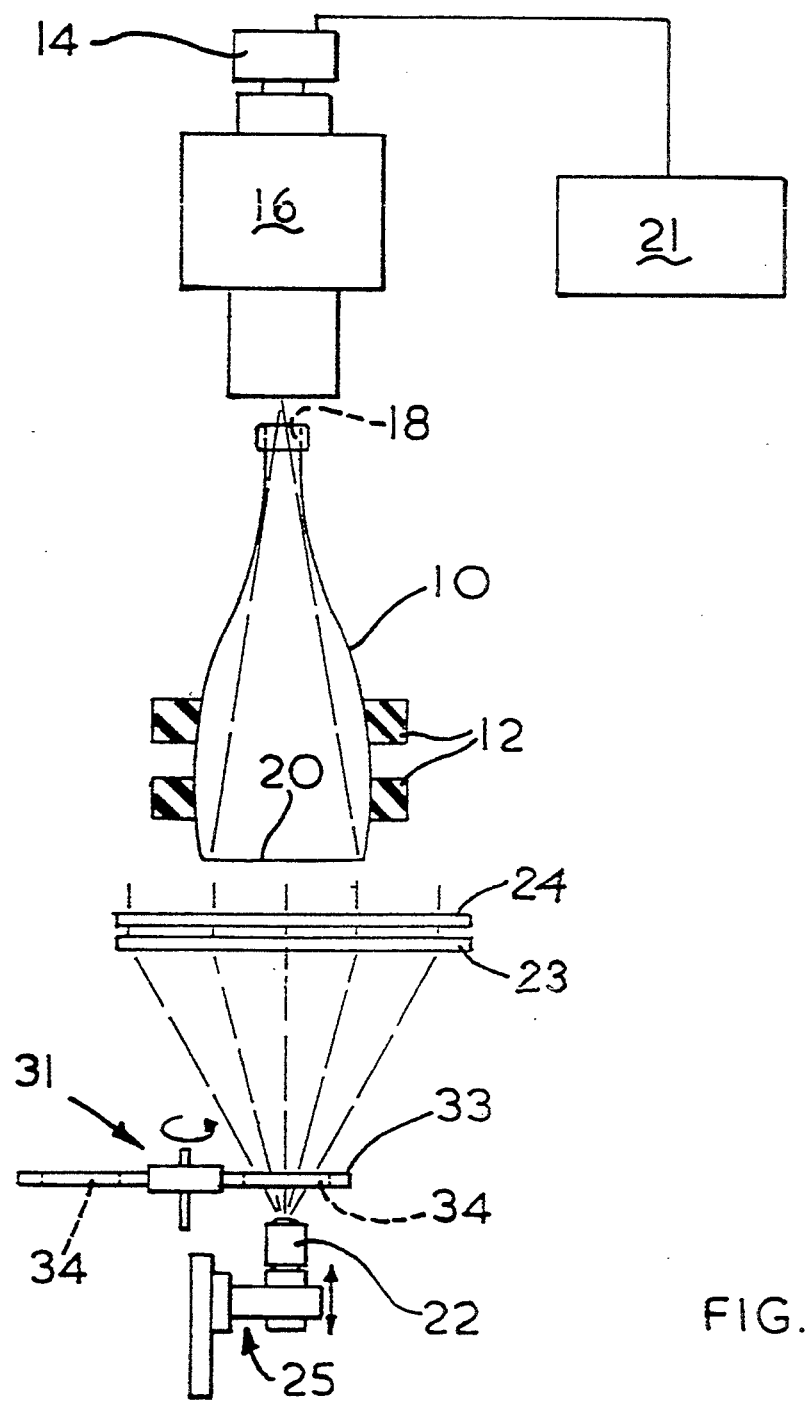
FIG. 1 is a side view of the bottom inspection device made in accordance with the teachings of the present invention.

A bottle 10 which is being conventionally displaced at a constant speed by opposed pairs of belts 12 passes through a bottom inspection station where an image is sensed on the imaging surface of a two dimensional camera 14 looking through a lens 16 and through the opening 18 of the bottle at the bottom 20 of the bottle. This data is evaluated by a computer 21.

A high quality diffuse backlight is provided using a point source 22 (here an arc or gas discharge lamp which provides a white light which will be strobed), a collimating lens 23 (in this case a Fresnel lens for compactness and low cost) and a non-Lambertian diffusing element 24. This diffused light is uniform in brightness over the entire surface of the diffusing element, and the variation in brightness with angle is uniform over the entire surface. This source will work well with most bottles and lenses, however, wide angle lenses positioned near the source (as with a wide bottom short bottle) will see the light level fall off toward the edges of the light source. This effect will compound the problem of viewing a colored bottle with a relatively thicker heel section. By attaching the source to a mounting 25 movable with respect to the lens, the position of the light source which is nominally equal to one focal length behind the lens can be moved away from the lens so the diffuse rays away from the center of the bottom will be skewed toward the axis and toward the lens aperture.

This effect can be tailored to the working distance of the lens for a particular bottle to insure no light falloff even at close working distance and wide viewing angles. An appropriate adjustment will help illuminate the heel sections of colored bottles with heavy heels such as champagne bottles. The diffusing element 24 may be a sheet of glass having a ground surface (ground glass) or it may be a variable diffusing element where the degree of diffusion can be selectively varied.

A Lambertian light source, used to light bottle bottoms, will cause refractive artifacts in the bottle bottom, such as molded lettering, to be rendered with so little contrast as to be essentially invisible to the camera and computing system. This can be at times an advantage. However, it will also cause tramp glass (fragments of glass within the bottle) to be rendered with very little contrast, making it difficult to catch this class of defect. Therefore, a degree of control of the contrast is provided to optimally illuminate a particular bottle and class of defects.

To provide a wide range of diffusion from slight (highly directional) to nearly Lambertian (perfectly diffuse, no direction) variable diffusing elements are provided.

Figure 2A:
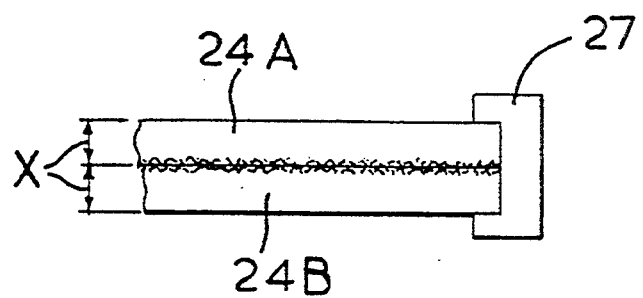
FIGS. 2a, 2b and 2c are side views illustrating a diffusing element made up of two ground glass plates which can be selectively related to alter the diffusion.
Figure 2B:
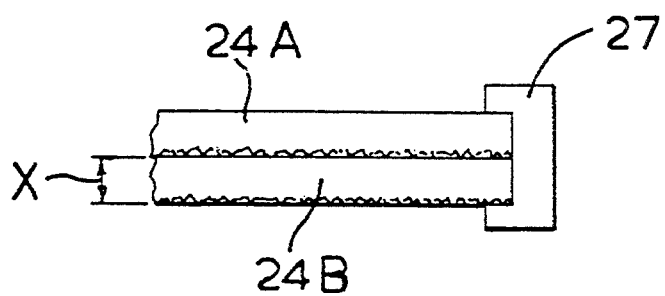
Figure 2C:
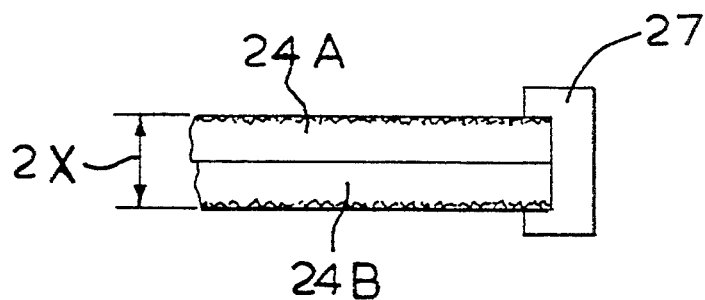
Figure 3:
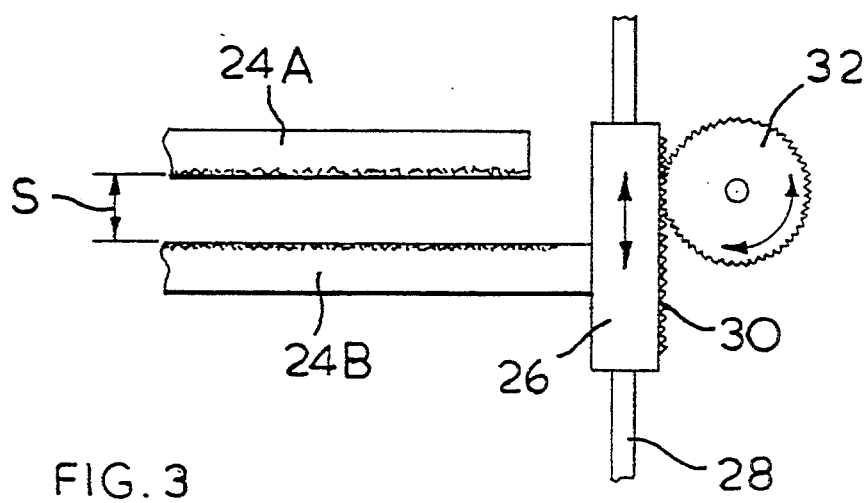
FIG. 3 is a side view of an alternate variable diffusing element.

The variable diffusing element shown in FIGS. 2A–C is made up of a pair of ground glass sheets supported by a clamping device 27. When the ground glass surfaces are adjacent as shown in FIG. 2A the degree of diffusion is basically that resulting from one of the ground glass sheets. When the two ground glass sheets are arranged so that both ground glass surfaces are on the same side (right hand) of the ground glass sheets (FIG. 2B) the ground glass surfaces will be separated by the thickness X of the sheets. This separation can be set at 2X by locating these surfaces on the outside surfaces of the diffusion element as shown in FIG. 2C. To have greater control of this variation one of the sheets 24B (FIG. 3) can be secured to an element 26 which is displaceable along a slide 28. For example, the displaceable element 26 can be keyed to a slide 28 and have a rack 30 engageable by a pinion 32 rotatable by hand or under the automatic control of a servo motor or the like. This same displacement mechanism could also be used to displace the light source.

The objective of a bottom inspection device is to accept all of the refractive, dispersive and absorptive artifacts which are characteristic of a good bottle while rejecting all the same type of artifacts which are characteristic of bottle defects. A good bottle may have a wide disparity of thicknesses in the base. If the bottle is heavily colored, this may present a dynamic brightness range beyond the capabilities of the camera.

The extinction of illumination rays traversing the bottom of the bottle is dependent on the spectral absorption of the glass as well as the spectral composition of the light. In the embodiment shown in FIG. 1, spectral composition of the light is matched to spectral absorption of the bottle glass, so that it will undergo relatively less extinction and thereby present a lower contrast image to the camera. (The overall intensity may have to be increased to account for the loss in filtering, but the contrast will still be reduced and may be made to be within the dynamic range of the camera.) To this end, a selectable color filter 30 is provided which includes a disc 32 supporting a plurality of filters 34 matched to the glass to be inspected (light and dark yellow, light and dark green, brown and flint, for example) which is rotatably mounted so that the filter which has a color matching the bottle can be located above the point light source. Alternatively, suitably colored acetate sheets could be placed on top of the variable diffuser.

I claim:

1. A machine for inspecting the bottom of a glass container having an opening at the top thereof comprising means for delivering a glass container to an inspection station, said inspection station including
        a two dimensional camera having an imaging surface,
    means for viewing the bottom of the glass container through the opening thereof and focusing the viewed bottom on said imaging surface,
    computer means for evaluating the viewed bottom imaged on said imaging surface and
    means for illuminating the bottom of the glass container including
        a source of light,
        a Fresnel lens for collimating light from said light source, and
        means for diffusing said collimated light including
            two glass sheets each having a diffusing surface, and
            means for supporting said two glass sheets in parallel relation, said supporting means including means for displacing one of said sheets to define a selected spacing therebetween.

2. A machine for inspecting the bottom of a glass container according to claim 1, further comprising means for displacing said light source to define a selected spacing between said light source and said Fresnel lens.

3. A machine for inspecting the bottom of a glass container according to claim 1, further comprising means for filtering the light from said light source with a colored filter corresponding to the color of the glass container.

4. A machine for inspecting the bottom of a glass container according to claim 1, wherein said filtering means comprises a rotatable member supporting a plurality of different filtering means selectively locatable to filter the light from said light source.

5. A machine for inspecting the bottom of a glass container according to claim 1, further comprising means for clamping said two parallel glass sheets together so that the ground surfaces of said sheets can be adjacent, separated by one of said sheets or separated by both of said sheets.

6. A machine for inspecting the bottom of a glass container according to claim 1 wherein each of said diffusing surfaces is a ground surface.

* * * * *